United States Patent [19]

Graham

[11] Patent Number: 4,665,090

[45] Date of Patent: May 12, 1987

[54] SUBSTITUTED THIOPHENE-2-SULFONAMIDE ANTIGLAUCOMA AGENTS

[75] Inventor: Samuel L. Graham, Harleysville, Pa.

[73] Assignee: Merck & Co., Inc., Rahway, N.J.

[21] Appl. No.: 785,830

[22] Filed: Oct. 9, 1985

[51] Int. Cl.$^4$ .................... A61K 31/38; C07D 333/32; C07D 409/00
[52] U.S. Cl. .................................. 514/445; 514/336; 549/65; 546/284
[58] Field of Search ............... 549/66, 65, 8; 544/379, 544/146; 546/212, 284; 514/445, 336

[56] References Cited

U.S. PATENT DOCUMENTS 3,991,081  11/1978  Edwards .
4,264,774  4/1981   Goralski .

FOREIGN PATENT DOCUMENTS 0042731  12/1981  European Pat. Off. ............... 549/65
7011219  2/1971   Netherlands ........................... 549/65

*Primary Examiner*—Alan Siegel
*Attorney, Agent, or Firm*—William H. Nicholson; Michael C. Sudol

[57] ABSTRACT

Thiophene-2-sulfonamides with a 5-alkyl-substituent are carbonic anhydrase inhibitors useful in the treatment of elevated intraocular pressure.

12 Claims, No Drawings

SUBSTITUTED THIOPHENE-2-SULFONAMIDE ANTIGLAUCOMA AGENTS

SUMMARY OF THE INVENTION

This invention relates to novel thiophene-2-sulfonamides useful in the treatment of elevated intraocular pressure. More particularly this invention relates to compounds having the structural formula:

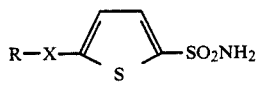

wherein R and X are hereinafter defined, as well as the pharmaceutically and ophthalmologically acceptable salts thereof. This invention also relates to pharmaceutical compositions and the use thereof for systemic and topical, optical administration employing a novel compound of this invention as active ingredient for the treatment of elevated intraocular pressure, especially when accompanied by pathological damage such as in the disease known as glaucoma.

BACKGROUND OF THE INVENTION

Glaucoma is an ocular disorder associated with elevated intraocular pressures which are too high for normal function and may result in irreversible loss of visual function. If untreated, glaucoma may eventually lead to blindness. Ocular hypertension, i.e., the condition of elevated intraocular pressure without optic nerve head damage or characteristic glaucomatous visual field defects, is now believed by many ophthalmologists to represent the earliest phase of glaucoma.

Many of the drugs formerly used to treat glaucoma proved not entirely satisfactory. Indeed, few advances were made in the treatment of glaucoma since pilocarpine and physostigmine were introduced. Only recently have clinicians noted that many β-adrenergic blocking agents are effective in reducing intraocular pressure. While many of these agents are effective in reducing intraocular pressure, they also have other characteristics, e.g. membrane stabilizing activity, that render them unacceptable for chronic ocular use. (S)-1-tert-Butylamino-3-[(4-morpholino-1,2,5-thiadiazol-3-yl)oxy]-2-propanol, a β-adrenergic blocking agent, was found to reduce intraocular pressure and to be devoid of many unwanted side effects associated with pilocarpine and, in addition, to possess advantages over many other β-adrenergic blocking agents, e.g. to be devoid of local anesthetic properties, to have a long duration of activity, and to display minimal tolerance.

Although pilocarpine, physostigmine and the β-blocking agents mentioned above reduce intraocular pressure, none of these drugs manifests its action by inhibiting the enzyme carbonic anhydrase and, thereby, impeding the contribution to aqueous humor formation made by the carbonic anhydrase pathway.

Agents referred to as carbonic anhydrase inhibitors, block or impede this inflow pathway by inhibiting the enzyme, carbonic anhydrase. While such carbonic anhydrase inhibitors are now used to treat intraocular pressure by oral, intravenous or other systemic routes, they thereby have the distinct disadvantage of inhibiting carbonic anhydrase throughout the entire body. Such a gross disruption of a basic enzyme system is justified only during an acute attack of alarmingly elevated intraocular pressure, or when no other agent is effective. Despite the desirability of directing the carbonic anhydrase inhibitor only to the desired ophthalmic target tissue, no topically effective carbonic anhydrase inhibitors are available for clinical use.

However, topically effective carbonic anhydrase inhibitors are reported in U.S. Pat. Nos. 4,386,098; 4,416,890; 4,426,388; and 4,510,155. The compounds reported therein are 5 (and 6)-hydroxy-2-benzothiazolesulfonamides and acyl esters thereof.

To be an effective and acceptable topical agent, an ophthalmic carbonic anhydrase inhibitor must not only penetrate the ophthalmic tissues to reach the active sites within the eye, but it must also be devoid of those side effects including irritation, allergic reaction and the like which would militate against long term administration.

DETAILED DESCRIPTION OF THE INVENTION

The novel compounds of this invention have structural formula:

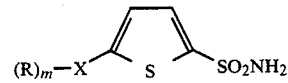

or an ophthalmologically acceptable salt thereof, wherein

X is a straight, branched or cyclic, saturated or unsaturated hydrocarbon of up to 10 carbon atoms, such as

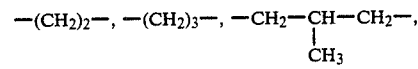

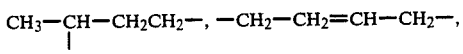

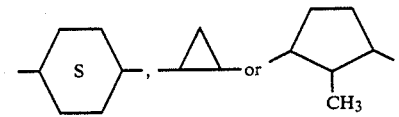

m is 1 or 2;
R is
(1) —OR$^1$ wherein R$^1$ is
  (a) hydrogen,
  (b) $C_{1-4}$ alkyl,
  (c) hydroxy-$C_{1-4}$ alkyl,
  (d) $C_{1-4}$ alkoxy-$C_{1-4}$ alkyl,
  (e) phenyl,
  (f) pyridyl,
  (g) carboxy-$C_{1-4}$ alkyl,
  (h) ω-amino-ω-carboxy-$C_{1-4}$ alkyl;

 (2)

 (3)

 (4)

-continued

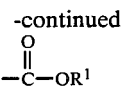 (5)

(6) —N(R$^1$)$_2$ wherein the R$^1$ groups are the same or different, or can be joined together to form, with the nitrogen atom to which they are attached, a 5- or 6-membered heterocycle such as piperidino, piperazino, morpholino, 1-pyrrolyl, or the like.

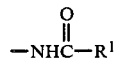 (7)

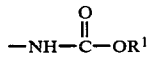 (8)

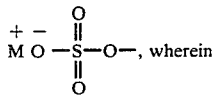 (9)

wherein

M+ is an ophthalmologically acceptable cation selected from sodium, potassium ammonium, tetra(C$_{1-4}$alkyl)ammonium, pyridinium, imidazolium, pralidoxime, and thiamine

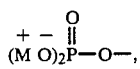 (10)

wherein M+ is as previously defined;

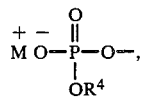 (11)

wherein R$^4$ is C$_{1-3}$ alkyl or phenyl —C$_{1-3}$ alkyl; or

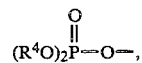 (12)

wherein R$^4$ is as previously defined, and the two may be the same or different.

It is preferred that X be —(CH$_2$)$_{1-6}$—.

Specific compounds within the scope of this invention are:
5-(2-hydroxyethyl)thiophene-2-sulfonamide
5-(2,3-dihydroxypropyl)thiophene-2-sulfonamide
5-(trans-4-hydroxycyclohexyl)thiophene-2-sulfonamide
5-(2-acetoxyethyl)thiophene-2-sulfonamide
5-(3-hydroxypropyl)thiophene-2-sulfonamide In a novel process of this invention the alkylthiophene is treated with at least a molar equivalent of n-butyl lithium in an inert solvent such as tetrahydrofuran at a reduced temperature, preferably below −10° C., most suitably at −70° C. Sulfur dioxide gas is then passed over the solution at a rate such that the reaction mixture does not exceed a temperature of −10° C. After the reaction is complete, the solvents are removed to provide the lithium thiophene-2-sulfinate. This intermediate is then reacted with N-chlorosuccinimide at temperatures generally below 0° C. to produce the corresponding thiophene sulfonyl chloride.

Alternatively, the product from the treatment of the thiophene with N-butyl lithium can be treated with sulfuryl chloride in an inert solvent such as hexane at about −70° C. followed by warming to room temperature.

A second alternative involves the use of an electrophilic sulfonating agent such as sulfuric acid and acetic anhydride in ethyl acetate at about ice-bath temperature followed by addition of a weak base such as potassium acetate to provide the sulfonate salt. Chlorination with an agent such as oxalyl chloride, thionyl chloride or phosphorus oxychloride provides the thiophene sulfonyl chloride.

In each case the thiophene-2-sulfonamide is prepared by treating the sulfonyl chloride with concentrated aqueous ammonia.

A third alternative process of this invention comprises the treatment of lithium thiophene-2-sulfinate with hydroxylamine-O-sulfonic acid to produce the corresponding sulfonamide.

The process is conducted in aqueous medium at temperature between about 0° C. and 35° C. Although a higher temperature may be employed it is unnecessary and may result in lower yields and potentially violent reactions. The reaction proceeds quickly and exothermically so that only a few minutes are required but times of up to several hours are not detrimental.

Following either process for introduction of the sulfonamide, hydroxyl protecting groups may be removed by acid or base hydrolysis, depending on the nature of the group, to produce the free hydroxyl.

The process to prepare those compounds wherein R is

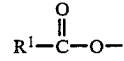

is represented by the following reaction scheme:

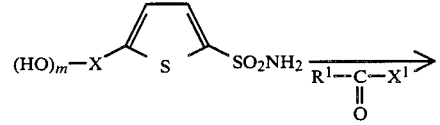

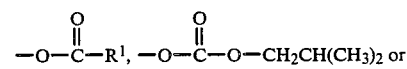

where R$^1$ has the meanings hereinbefore designated, and X$^1$ is chloro, bromo, iodo,

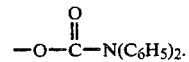

Generally equimolar amounts of the thiophene and

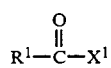

are employed, although use of an excess of the more readily available reactant is satisfactory.

The reaction is conducted in a suitable, inert solvent such as acetone, dimethylformamide, pyridine, ethyl acetate, tetrahydrofuran or benzene and the like with at least an equimolar amount of a hydrohalide acceptor when the acylating agent is an acyl halide or with a carboxylic acid acceptor when the acylating agent is an acid anhydride. Bases such as triethylamine, pyridine and the like may be employed for this purpose.

The reaction may be conducted with or without a catalyst at temperatures of from 0° C. to the boiling point of the solvent used but preferably from about 15° C. to 50° C.

When a catalyst is employed, a 4,4-dialkylaminopyridine such as 4-dimethylaminopyridine or 4-pyrrolidinopyridine is preferred.

The compounds wherein R is

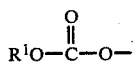

of this invention are most suitably prepared by reacting a compound of structure:

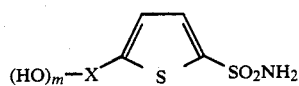

with an appropriate haloformate, particularly a chloroformate of the formula:

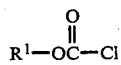

or a bis carbonate of the formula:

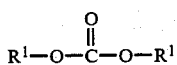

The reaction is conducted in a suitable solvent such as dimethylformamide, pyridine, acetone, ethyl acetate, tetrahydrofuran or benzene and the like with at least an equimolar amount of a hydrohalide acceptor. Bases such as triethylamine, pyridine and the like may be employed for this purpose.

The reaction may be conducted with or without a catalyst at temperatures of from 0° C. to the boiling point of the solvent used but preferably from 15° C. to 50° C.

When a catalyst is employed, triethylamine or a 4,4-dialkylaminopyridine such as 4-dimethylaminopyridine or 4-pyrrolidinopyridine is preferred.

Another process of this invention for preparing the ethers, i.e. $R=OR^1$ wherein $R^1\neq H$, the hydroxy compound is treated with an "alkylating" agent of formula $R^1-X^2$ wherein $X^2$ is a halide such as chloride, bromide or iodide, or other good leaving group such as mesylate, tosylate or benzenesulfonate in a suitable solvent such as dimethylformamide, hexamethylphosphoramide, or the like in the presence of a base such as an alkali metal alkoxide, preferably sodium methoxide, at about 0° C. to 35° C., usually about room temperature for about 10 to 30 hours.

The O-sulfates of this invention are prepared by reacting an hydroxyalkylthiophene-2-sulfonamide with sulfamic acid in pyridine at elevated temperatures (about 50° C. to the boiling point) for about 18 to 48 hours to provide the ammonium salt followed, if desired, by titration with hydroxides of the formula MOH to provide the other salts.

Similarly the O-phosphates of this invention are prepared by treatment of a hydroxy compound with phosphorus oxychloride, an alkyl dichlorophosphate or a dialkyl chlorophosphate in pyridine or similar basic solvent at about −5° to +5° C. for about 0.25 to 1.0 hour.

The novel pharmaceutical formulations of this invention include formulations for systemic administration and ophthalmic formulations designed for topical ocular administration, preferably the latter.

The formulations for systemic administration comprise a non-toxic pharmaceutically acceptable carrier and an effective amount of one or more of the novel compounds of this invention. They may be in a form (a) for oral administration; e.g., as tablets, in combination with other compounding ingredients customarily used such as talc, vegetable oils, polyols, benzyl alcohols, gums, gelatin, starches and other carriers; dissolved or dispersed or emulsified in a suitable liquid carrier; in hard or soft capsules, encapsulated in a suitable material; or (b) for parenteral administration; e.g., dissolved or dispersed in a suitable liquid carrier as a solution, suspension or emulsion, or (c) for transdermal application, e.g. as a patch.

The active drugs of this invention are most suitably administered in the form of ophthalmic pharmaceutical compositions adapted for topical administration to the eye such as a solution, suspension, ointment, or as a solid insert. Formulations of these compounds may contain from 0.01 to 15% and especially 0.5% to 2% of medicament. They may contain a novel compound of this invention as the sole medicament or may contain as well an effective amount of a β-adrenergic blocking agent such as timolol maleate or a parasympathomimetic agent such as pilocarpine. The two active principles are present in approximately equal amounts on a weight basis.

The pharmaceutical preparation which contains the active compound may be conveniently admixed with a non-toxic pharmaceutical inorganic or organic carrier. Typical of pharmaceutically acceptable carriers are, for example, water, mixtures of water and water-miscible solvents such as lower alkanols or aralkanols, vegetable oils, polyalkylene glycols, petroleum based jelly, ethyl cellulose, ethyl oleate, carboxymethylcellulose, polyvinylpyrrolidone, isopropyl myristate and other conventionally employed acceptable carriers. The pharmaceutical preparation may also contain non-toxic auxiliary substances such as emulsifying, preserving, wetting agents, bodying agents and the like, as for example, polyethylene glycols 200, 300, 400 and 600, carbowaxes 1,000, 1,500, 4,000, 6,000 and 10,000, antibacterial components such as quaternary ammonium compounds, phenylmercuric salts known to have cold sterilizing properties and which are non-injurious in use, thimerosal, methyl and propyl paraben, benzyl alcohol, phenyl ethanol, buffering ingredients such as sodium chloride, sodium borate, sodium acetates, gluconate buffers, and other conventional ingredients such as sorbitan monolaurate, triethanolamine, polyoxyethylene sorbitan monopalmitylate, dioctyl sodium sulfosuccinate, monothioglycerol, thiosorbitol, ethylenediamine tetraacetic acid, and the like. Additionally, suitable ophthalmic vehicles can be used as carrier media for the present purpose including conventional phosphate buffer vehicle systems, isotonic boric acid vehicles, isotonic sodium chloride vehicles, isotonic sodium borate vehicles and the like.

The pharmaceutical preparation may also be in the form of a solid insert such as one which after dispensing the drug remains essentially intact, or a bio-erodible insert that either is soluble in lacrimal fluids, or otherwise disintegrates.

Generally, doses of the present compounds of about 0.01 to about 50 mg/kg and preferably from about 0.1 to about 20 mg/kg of body weight per day may be used. Dosage may be single or multiple depending on the daily total required and the unit dosage.

EXAMPLE 1

5-(2-Hydroxyethyl)thiophene-2-sulfonamide

Step A: Preparation of 2-(2-tetrahydropyranyloxyethyl)thiophene

A solution of 12.7 g of 2-(2-hydroxyethyl)-thiophene (0.099 mol) and 11.0 ml of dihydropyran (0.120 mol) was prepared in 125 ml of dry methylene chloride. Dry HCl gas was bubbled through the stirred mixture for approximately 15 seconds. After the mixture was allowed to stand for 24 hours, it was washed with saturated sodium bicarbonate and brine, and dried over $Na_2SO_4$. Evaporation of the solvent left 21.0 g (100%) of the protected alcohol which was used without purification in the next step.

Step B: Preparation of 5-(2-tetrahydropyranyloxy)thiophene-2-sulfonamide

The thiophene from Step A (5.00 g, 23.6 mmol) was dissolved in 20 ml of dry THF and cooled to 0°–5° C. A 1.6M solution of n-butyl lithium in hexane (15.8 ml, 25 mmol) was added dropwise with stirring over a 15 minute period and the resulting solution was stirred for 45 minutes at 0° C. The thienyl lithium reagent so generated was added by means of a stainless steel cannula to a solution of 1.90 ml of sulfuryl chloride (23.6 mmol) in 30 ml of hexane maintained at −70° C. The mixture was allowed to warm to room temperature and then concentrated on a rotary evaporator. The residue was dissolved in a small amount of acetone. This mixture was added to a stirred solution of 20 ml of concentrated $NH_4OH$ in 100 ml of acetone. After 30 minutes the solvents were evaporated and the products partitioned between 0.5N NaOH and ether. The aqueous phase was acidified and extracted with ethyl acetate. The organic phase was dried ($Na_2SO_4$) and evaporated to give 2.18 g of a yellow oil. The oil was chromatographed on 20 g of Florisil with 1:1 ethyl acetate/hexane. Those fractions containing the pure product by TLC analysis (silica gel, 1:1 ethyl acetate/hexane, $R_f$=0.36) were combined. Addition of hexane caused the product to crystallize. The white solid obtained weighed 1.20 g, m.p. 90°–92° C.

Analysis calc'd for $C_{11}H_{17}NO_4S_2$: N, 4.81; C, 45.34; H, 5.88; Found: N, 5.01; C, 45.66; H, 5.83.

Step C: Preparation of 5-(2-hydroxyethyl)thiophene-2-sulfonamide

The sulfonamide from Step B (1.00 g, 3.4 mmol) was dissolved in 30 ml of methanol and 2 drops of concentrated HCl was added. The course of the reaction was monitored by TLC (silica gel 1:1 ethyl acetate/hexane). Starting material $R_f$=0.36; Product $R_f$=0.09). After 5 hours the reaction was complete and the solution was basified with concentrated $NH_4OH$. The solvents were evaporated in vacuo and the residue was partitioned between ethyl acetate and water. The organic extract was washed with brine and dried ($Na_2SO_4$). Evaporation of the solvent gave 0.70 g of a white solid, m.p. 70°–72° C. The solid was powdered and slurried with ether. The product isolated by filtration, weighed 0.49 g, m.p. 73°–74° C.

Analysis calc'd for $C_6H_9NO_3S_2$: N, 6.76; C, 34.77; H, 4.38; Found: N, 6.49; C, 35.19; H, 4.45.

EXAMPLE 2

5-(4-Hydroxybutyl)thiophene-2-sulfonamide

Step A: Preparation of 2-(4-hydroxybutyl)thiophene

To a cool (0°) solution of 10.0 g of 4-thienylbutyric acid (58.8 mmol) in 60 ml of dry THF was added 59 ml of a 1M solution of borane in THF, dropwise with stirring over one hour. The mixture was stirred for an additional 5 hours. The reaction mixture was poured onto 200 g of ice. This mixture was acidified with 2N HCl and the product extracted into ethyl acetate. The extract was washed with brine, dried ($Na_2SO_4$) and evaporated to give 8.5 g of a colorless oil (93%). $^1$H-NMR (CDCl$_3$)δ7.0 (1H, t); 6.75 (2H, m); 3.5 (2H, t); 2.75 (2H, t); 1.6 (4H, m).

Step B: Preparation of 2-(4-acetoxybutyl)thiophene

The crude product from Step A was dissolved in 100 ml of THF and the mixture was cooled in an ice-water bath. Triethylamine (7.5 ml, 54 mmol) was added followed by dropwise addition of 3.8 ml of acetyl chloride (54 mmol). The mixture was allowed to stir overnight at ambient temperature. The solution was filtered and concentrated on a rotary evaporator. The residue was partitioned between ethyl acetate and dilute, cold 1N HCl. The organic phase was washed with saturated $NaHCO_3$ solution, brine and then dried ($Na_2SO_4$). Evaporation of the solvent left 10.48 g of the desired acetate (98%) the solvent left 10.48 g of the desired acetate (98%) as a light yellow oil. $^1$H-NMR (CDCl$_3$)δ7.2–6.6 (3H, m); 2.9 (2H, t); 2.45 (2H, t); 2.15 (3H, s); 2.0 (4H, m).

Step C: Preparation of potassium 5-(4-acetoxybutyl)-thiophene-2-sulfonate

The crude product from Step B (53 mmol) was dissolved in 50 ml of ethyl acetate and cooled to 0° C. in an ice-water bath. Acetic anhydride (10.0 ml, 106 mmol) was added followed by the dropwise addition of a solution of sulfuric acid (3.0 ml, 54 mmol) in 18 ml ethyl acetate. The mixture was stirred for 2 hours at ice-bath temperature. A solution of potassium acetate (5.19 g, 53 mmol) in a minimum volume of 95% ethanol was then added dropwise with stirring. After 30 minutes the sulfonate salt was isolated by suction filtration.

Step D: Preparation of 5-(4-hydroxybutyl)thiophene2-sulfonamide

The crude potassium salt prepared from Step C was suspended in 150 ml of ethyl acetate and the mixture was cooled in an ice-water bath. Oxalyl chloride (13.9 ml, 159 mmol) was added dropwise with stirring over 30 minutes. Gas evolution occurred during the addition. A solution of 1.9 ml of DMF (25 mmol) in 10 ml ethyl acetate was then added dropwise with stirring over 30 minutes. A vigorous gas evolution was observed. The cooling bath was removed, and stirring was continued for 18 hours. The mixture was chilled in an ice-water bath and 10 ml ice-cold water was added cautiously. The phases were separated and the organic phase washed with brine and dried ($Na_2SO_4$). The drying agent was removed by filtration and the ethyl acetate solution was cooled in an ice bath. Concentrated ammonium hydroxide (20 ml) was added and the heterogeneous mixture was stirred vigorously for 2 hours. The solvents were evaporated in vacuo, and the residue was partitioned between 1N HCl and ethyl acetate. The organic phase was washed with brine and dried (Na$_2$SO$_4$). Evaporation of the solvent gave 6.35 g of a mixture of the desired product and its O-acetyl derivative. The mixture was dissolved in 100 ml of 1N NaOH and stirred for 1 hour and then acidified with concentrated HCl. The aqueous solution was extracted with ethyl acetate and the extract was washed with brine and dried. Evaporation gave 5.80 g of a viscous yellow oil. A portion of this oil weighing 1.58 g was adsorbed on silica and placed on a 30 g silica gel column. The compound was eluted with ethyl acetate/hexane on a gradient from 1:1 to 2:1. Fractions containing the desired material were combined and evaporated giving 1.40 g of an oil which solidified upon standing overnight, m.p. 50°–53° C. The material was redissolved in 10 ml of ethyl acetate and hexane was added until just turbid. A few drops of ethyl acetate were added to obtain a clear solution and the mixture was allowed to slowly evaporate. After approximately one-half of the solvent had evaporated the crystalline product (0.51 g) was isolated by suction filtration, m.p. 51°–53° C. $^1$H-NMR (CDCl$_3$+DMSO-d$_6$)δ7.45 (1H, d); 7.1 (2H, s); 6.76 (1H, d); 3.56 (2H, t); 2.84 (2H, t); 1.75 (2H, m); 1.60 (2H, m).

Analysis calc'd for C$_8$H$_{13}$NO$_3$S$_2$: C, 40.83; H, 5.57; N, 5.95; Found: C, 41.06; H, 5.77; N, 5.93.

Acetylation of the product from Example 2, Step D with acetic anhydride and pyridine in ethyl acetate provided 5-(4-acetoxybutyl)thiophene-2-sulfonamide, m.p. 75°–77° C.

Employing the procedure substantially as described in Example 2, Steps C and D but starting with 2-(4-oxopentyl)thiophene there is produced 5-(4-oxopentyl)-thiophene-2-sulfonamide, m.p. 54°–57° C. (partial melt and resolidification) 64°–65° C.

EXAMPLE 3

5-(4-Hydroxypentyl)thiophene-2-sulfonamide

Step A: Preparation of 2-(4-hydroxypentyl)thiophene 2-(4-Oxopentyl)thiophene (3.30 g, 19.6 mmol) was dissolved in 10 ml of 95% ethanol and the solution was added to a stirred solution of sodium borohydride (0.38 g, 10 mmol) in 20 ml of ethanol at room temperature. The mixture was stirred overnight and the excess reducing agent destroyed by the dropwise addition of 1N HCl. The solvents were evaporated and the residue partitioned between water and ether. The organic phase was washed with water and brine and dried (Na$_2$SO$_4$) Evaporation of the solvents gave 3.13 g of product as a yellow oil, which was used without purification in the next step.

Step B: Preparation of 2-(4-Tetrahydropyranyloxypentyl)thiophene

By the procedure described in Example 1, Step A, the alcohol prepared above was converted to the tetrahydropyranyl ether, as a mixture of diastereomers. $^1$H-NMR (CDCl$_3$)δ: 7.12 (1H, m); 6.94 (1H, m); 4.73 and 4.62 (1H, m); 3.72–4.00 (2H, m); 3.50 (1H, m); 2.86 (2H, q); 1.95–1.40 (10H, m); 1.25 and 1.13 (3H, d).

Step C: Preparation of 5-(4-hydroxypentyl)thiophene2-sulfonamide

A solution of the product prepared in Step B (18 mmol) in 30 ml of THF was cooled in an ice bath and 10 mg of bipyridyl was added as an indicator. A solution of n-butyl lithium (1.5M in hexane, 15 ml, 22 mmol) was added dropwise over 20 minutes and the mixture stirred for 2 hours at 0° C. After cooling to −40° C., sulfur dioxide gas was introduced to the reaction vessel until the red color of the indicator was discharged. The cooling bath was removed and stirring was continued for 2 hours. The solvents were evaporated. The residue was dissolved in 50 ml of water and 5.4 g of sodium acetate trihydrate was added. Hydroxylamine-O-sulfonic acid (2.26 g, 20 mmol) was added and the mixture was stirred for 19 hours. The mixture was extracted with ethyl acetate and the extract was washed with water and brine. After drying (Na$_2$SO$_4$) the solvent was evaporated leaving 7.2 g of a yellow oil. The material was dissolved in 60 ml of THF and 20 ml of 1N HCl. The mixture was stirred at room temperature for 2 hours and at reflux for 2 hours. The mixture was cooled and evaporated and the residue was partitioned between ethyl acetate and water. The organic phase was washed with saturated sodium bicarbonate solution and brine. After drying (Na$_2$SO$_4$), 5.4 g of crude product was obtained. Chromatography on silica gave the pure compound (1.5 g) as an oil. $^1$H-NMR (DMSO-d$_6$)δ7.60 (br s, 2H); 7.41 (d, 1H); 6.91 (d, 1H); 4.44 (br s, 1H); 3.64 (m, 1H); 2.84 (t, 2H); 1.68 (m, 2H); 1.39 (m, 2H); 1.08 (d, 3H).

Analysis calc'd for C$_9$H$_{15}$NO$_3$S$_2$: C, 43.35; H, 6.06; N, 5.62; Found: C, 43.24; H, 6.24; N, 5.64.

Employing the procedures substantially as described in Steps B and C of Example 3 but starting with 2-(5-hydroxypentyl)thiophene there was produced in comparable yield 5-(5-hydroxypentyl)thiophene2-sulfonamide, m.p. 65°–67° C.

EXAMPLE 4

5-(5-Hydroxyhexyl)thiophene-2-sulfonamide

Step A: Preparation of 4-(2-thenoyl)butyric acid

Thiophene (19.5 ml) and glutaric anhydride (27.5 g) were mixed and heated to 60° C. under a nitrogen atmosphere until all solid dissolved. The heat was removed and 2.4 grams of 85% orthophosphoric acid was added. The reaction mixture was then heated to 100° C. for four hours, cooled, and 46 ml of water added. The mixture was extracted with ether then the ether phase was extracted with aqueous sodium hydroxide solution (2.5N). The aqueous phase was cooled and made acidic by addition of 6N hydrochloric acid. Solid which precipitated out was collected on a filter, washed with water and dried under vacuum at 60° C. Yield 9.2 g N.M.R. (CDCl$_3$)δ2.1 (m, 2H), 2.54 (t, 2H), 3.04 (t, 2H), 7.14 (t, 1H), 7.64 (dd, 1H), 7.74 (d, 1H).

Step B: Preparation of 5-(2-thienyl)pentanoic acid 4-(2-thenoyl)butyric acid (9.2 g) was dissolved in 60 ml of diethylene glycol and 30 ml of hydrazine hydrate added. After heating the mixture to 120° C. gradual addition of potassium hydroxide (13.6 g) was begun. Low boiling components were distilled out of the reaction mixture until the reaction mixture temperature reached 210° C. After cooling to room temperature water was added to the reaction mixture followed by 6N hydrochloric acid. This mixture was extracted with benzene, the benzene dried over sodium sulfate, filtered through a pad of charcoal, and concentrated under vacuum. A solid residue was obtained after trituration with ligroine, cooling and scratching. Yield 5.5 g. N.M.R. (CDCl$_3$)δ1.76 (m, 4H), 2.42 (m, 2H), 2.88 (m, 2H), 6.80 (m, 1H), 6.90 (m, 1H), 7.12 (m, 1H).

Step C: Preparation of 6-(2-thienyl-2-oxohexane)

Lithium hydride (0.30 g) was suspended in 50 ml of dry 1,2-dimethoxyethane and 5.5 g of 5-(2-thienyl)pentanoic acid added. This mixture was heated at reflux under a nitrogen atmosphere for 2 hours, cooled to 5° C. and 48 ml of 1.4M methyl lithium in ether added. The reaction mixture was stirred for 1.5 hours at room temperature then transferred slowly into a vigorously stirred mixture of 7.8 ml concentrated hydrochloric acid and 160 ml of water. The aqueous phase was saturated with sodium chloride, the organic phase separated and the aqueous phase was extracted with ether. All organic phases were combined, dried, and concentrated under vacuum to give 4.2 g of liquid residue. This oil was chromatographed to yield 3.2 g of oily product. N.M.R. (CDCl$_3$)$\delta$1.64 (m, 4H), 2.12 (s, 3H), 2.44 (t, 2H), 2.82 (t, 2H), 6.74 (d, 1H), 6.88 (t, 1H), 7.06 (dd, 1H).

Step D: Preparation of 5-(5-oxohexyl)thiophene-2-sulfonamide 4-(2-thienyl)-2-oxohexane (3.2 g) was dissolved in ethyl acetate (11 ml) and cooled in an ice bath. A cold mixture of 2.16 g of sulfuric acid in 6.8 ml of ethyl acetate was added and after 5 minutes a cold mixture of 3.60 g of acetic anhydride in 7 ml of ethyl acetate was added. After stirring for 45 minutes at ice bath temperature an alcoholic solution of 2.07 g of potassium acetate was added dropwise, causing a solid to precipitate. After stirring for 1 hour at 0° C. the solid was collected on a filter, washed with ethyl acetate and dried under vacuum to a weight of 4.83 grams. This solid was suspended in 45 ml of ethyl acetate, cooled in an ice bath and 2.9 ml of oxalyl chloride was added. After stirring for 15 minutes 0.62 ml of dimethyl formamide was added dropwise causing gas evolution. This reaction mixture was stirred for 16 hours at room temperature, cooled to 0° C., washed with brine, then added dropwise to cold concentrated ammonium hydroxide solution and stirred for 3½ hours. The reaction mixture was acidified, the organic phase separated, washed with brine, filtered through a pad of charcoal, and concentrated under vacuum to a yellow colored liquid. This liquid was dissolved in ether and extracted with 1N sodium hydroxide. The aqueous phase was separated, acidified and extracted with ether. This ether phase was separated, washed with brine, filtered through a pad of charcoal, and concentrated under vacuum to a yellow colored liquid. This liquid was dissolved in ether and extracted with 1N sodium hydroxide. The aqueous phase was separated, acidified and extracted with ether. This ether phase was separated, washed with brine, filtered through a pad of charcoal and concentrated under vacuum to give 1.7 grams of liquid residue. By N.M.R. this liquid was the desired product contaminated with ethyl acetate and acetic acid. N.M.R. (CDCl$_3$)$\delta$1.64 (m, 4H), 2.14 (s, 3H), 2.48 (t, 2H), 2.82 (t, 2H), 5.72 (bs, 2H), 6.72 (d, 1H), 7.42 (d, 1H).

Step E: Preparation of 5-(5-hydroxyhexyl)thiophene-2-sulfonamide 5-(5-oxohexyl)thiophene-2-sulfonamide (1.7 g) was dissolved in ethanol and 0.2 grams of sodium borohydride added. After 1 hour of stirring the reaction mixture was made acidic with 1N hydrochloric acid then concentrated under vacuum. This residue was treated with 1N hydrochloric acid to insure that no borate esters were present. The product was then extracted into ether, dried over sodium sulfate and concentrated under vacuum to give 1.3 grams of an oil plus solid mixture. This was chromatographed twice using 230–400 mesh gel and eluting with 0–10% methanol in chloroform providing 0.6 g of product which was recrystallized from water. m.p. 75°–76° C. N.M.R. (CDCl$_3$)$\delta$1.16 (d, 3H), 1.43 (m, 5H), 1.64 (m, 2H), 2.80 (t, 2H), 3.76 (m, 1H), 5.04 (bs, 2H), 6.69 (d, 1H), 7.42 (d, 1H), Analysis calculated for C$_{10}$H$_{17}$NO$_3$S$_2$: C, 45.60%; N, 5.32%; H, 6.51% and found: C, 45.41%; N, 5.53%; H, 6.63%.

EXAMPLE 5

5-(2-Aminoethyl)thiophene-2-sulfonamide hydrochloride

Step A: Preparation of N-(2-(2-thienyl)ethyl) phthalimide

N-Carboethoxyphthalimide (4.93 g, 22.5 mmol) was added to a solution of 2-(2-thienyl)ethylamine (2.75 g, 21.6 mmol) in ethanol (20 ml) and was stirred for 20–25 hours. The precipitated product was collected by filtration, washed with cold methanol and dried. The product obtained (5.45 g) was used in the next step without purification.

Step B: Preparation of N-(2-(5-sulfamoyl-2-thienyl)ethyl)phthalimide

To a mixture of N-(2-(2-thienyl)ethyl) phthalimide (4.92 g, 19.1 mmol) and acetic anhydride (5.5 ml, 58 mmol) in methylene chloride (30 ml) was added dropwise conc. sulfuric acid (1.2 ml, 20 mmol). After two hours, the reaction was diluted with diethyl ether (50 ml) and the precipitated product was collected by filtration.

This crude sulfonic acid (6.0 g) was suspended in methylene chloride (40 ml) and phosphorus pentachloride (5.4 g, 25.5 mmol) was added under a nitrogen atmosphere. A clear yellow solution was obtained after one hour. This solution was poured into ice-water and stirred for ½ hour. The organic layer was separated, washed with water and saturated sodium bicarbonate, dried over anhydrous sodium sulfate and evaporated to give crude sulfonyl chloride (6.3 g).

This intermediate was dissolved in acetone (50 ml) and a mixture of ammonium hydroxide (16 ml) and acetone (16 ml) was added dropwise. After two hours, the precipitated product was collected by filtration, washed with water, ethanol, and diethyl ether. Additional product was obtained by concentration of the filtrate. The combined crops (5.2 g) were crystallized from a large volume of acetonitrile to give pure title compound (4.8 g), m.p. 226–229° C.

Step C: Preparation 5-(2-Aminoethyl)thiophene-2-sulfonamide hydrochloride

To a solution of methylamine (9 g, 0.33 mol) in ethanol (40 ml), cooled in an ice bath, was added N-(2-(5-sulfamoyl-2-thienyl)ethyl)phthalimide (3.2 g, 9.5 mmol). After stirring for 20–25 hours, the precipitated by-product was removed by filtration. The filtrate was concentrated and diethyl ether was added to precipitate remaining by-product. This was collected on a filter. The filtrate was concentrated to dryness to give the product free base as an oil. This oil was dissolved in ethanol and 6N ethanolic HCl was slowly added as the product precipitated. The salt was twice recrystallized by dissolution in methanol and careful dilution with diethyl ether to give 1.3 g, m.p. 222°–224° C.

EXAMPLE 6

| | | |
|---|---|---|
| 5-(4-hydroxybutyl)thiophene-2-sulfonamide (I) | 1 mg. | 15 mg. |

| | | |
|---|---|---|
| Monobasic sodium phosphate.2H₂O | 9.38 mg. | 6.10 mg. |
| Dibasic sodium phosphate.12H₂O | 28.48 mg. | 16.80 mg. |
| Benzalkonium chloride | 0.10 mg. | 0.10 mg. |
| Water for injection q.s. ad. | 1.0 ml. | 1.0 ml. |

Compound I, phosphate buffer salts, and benzalkonium chloride are added to and dissolved in water. The pH of the composition is adjusted to 6.8 and diluted to volume. The composition is rendered sterile by ionizing radiation.

EXAMPLE 7

| | |
|---|---|
| 5-(2-hydroxyethyl)thiophene-2-sulfonamide (II) | 5 mg. |
| petrolatum q.s. ad. | 1 gram |

Compound II and the petrolatum are aseptically combined.

EXAMPLE 8

| | |
|---|---|
| 5-(2-hydroxyethyl)thiophene-2-sulfonamide | 1 mg. |
| Hydroxypropylcellulose q.s. | 12 mg. |

Ophthalmic inserts are manufactured from compression molded films which are prepared on a Carver Press by subjecting the powdered mixture of the above ingredients to a compressional force of 12,000 lbs. (gauge) at 300° F. for one to four minutes. The film is cooled under pressure by having cold water circulate in the platen. Ophthalmic inserts are then individually cut from the film with a rod-shaped punch. Each insert is placed into a vial, which is then placed in a humidity cabinet (88% R.H. at 30° C.) for two to four days. After removal from the humidity cabinet, the vials are stoppered and then capped. The vials containing the hydrate insert are then autoclaved at 250° F. for ½ hour.

EXAMPLE 9

| | |
|---|---|
| 5-(4-hydroxypentyl)thiophene-2-sulfonamide | 1 mg. |
| Hydroxypropyl cellulose q.s. ad. | 12 mg. |

Ophthalmic inserts are manufactured from a solvent cast film prepared by making a viscous solution of the powdered ingredients listed above using methanol as the solvent. The solution is placed on a Teflon plate and allowed to dry at ambient conditions. After drying, the film is placed in an 88% R.H. cabinet until it is pliable. Appropriately sized inserts are cut from the film.

EXAMPLE 10

| | |
|---|---|
| 5-(3-hydroxypropyl)thiophene-2-sulfonamide | 1 mg. |
| Hydroxypropylmethyl cellulose q.s. ad. | 12 mg. |

Ophthalmic inserts are manufactured from a solvent cast film which is prepared by making a viscous solution of the powdered blend of the above ingredients using a methanol/water solvent system (10 ml. methanol is added to 2.5 g. of the powdered blend, to which 11 ml. of water (in three divided portions) is added. The solution is placed on a Teflon plate and allowed to dry at ambient conditions. After drying, the film is placed in an 88% R.H. cabinet until it is pliable. Appropriately sized inserts are then cut from the film.

EXAMPLE 11

| | |
|---|---|
| 5-(2-hydroxyethyl)thiophene-2-sulfonamide | 1 mg. |
| Hydroxypropylmethyl cellulose q.s. ad. | 12 mg. |

Ophthalmic inserts are manufactured from compression molded films which are prepared on a Carver Press by subjecting the powdered mixture of the above ingredients to a compressional force of 12,000 lbs. (gauge) at 350° F. for one minute. The film is cooled under pressure by having cold water circulate in the platen. Ophthalmic inserts are then individually cut from the film with a punch. Each insert is placed into a vial, which is then placed in a humidity cabinet (88% R.H. at 30° C.) for two to four days. After removal from the humidity cabinet, the vials are stoppered and then capped. The vials containing the hydrated insert are then autoclaved at 250° F. for one-half hour.

It is highly preferred that the solid inserts of this invention are available for use by the patient in a pathogen free condition. Thus, it is preferred to sterilize the inserts and to insure against recontamination, the sterilization is preferably conducted after packaging. The best mode of sterilizing is to employ ionizing radiation including radiation emanating from Cobalt 60 or high energy electron beams.

What is claimed is:

1. A compound of structural formula:

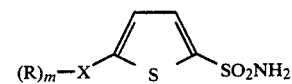

or an ophthalmologically acceptable salt thereof, wherein

X is a straight, branched, cyclic, saturated or unsaturated hydrocarbon of up to 10 carbons;

m is 1 or 2; and

R is (1) —OR¹ wherein R¹ is
 (a) hydrogen,
 (b) C₁₋₄ alkyl,
 (c) hydroxy-C₁₋₄ alkyl,
 (d) C₁₋₄ alkoxy-C₁₋₄ alkyl,
 (e) phenyl,
 (f) pyridyl
 (g) carboxy-C₁₋₄ alkyl,
 (h) ω-amino-ω-carboxy-C₁₋₄ alkyl;

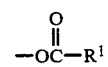   (2)

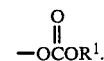   (3)

2. The compound of claim 1, wherein X is —(CH₂)₁₋₆—.

3. The compound of claim 2 wherein R is —OH and m is 1.

4. The compound of claim 3 which is:

5-(2-hydroxyethyl)thiophene-2-sulfonamide;
5-(4-hydroxybutyl)thiophene-2-sulfonamide;
5-(4-acetoxybutyl)thiophene-2-sulfonamide;
5-(4-hydroxypentyl)thiophene-2-sulfonamide;
5-(5-hydroxypentyl)thiophene-2-sulfonamide; or
5-(5-hydroxyhexyl)thiophene-2-sulfonamide.

5. An ophthalmological composition comprising an ophthalmologically acceptable carrier and an effective intraocular pressure lowering amount of a compound as defined in claim 1.

6. The composition of claim 5 wherein the compound is as defined in claim 2.

7. The composition of claim 5 wherein the compound is as defined in claim 3.

8. The composition of claim 5 wherein the compound is as defined in claim 4.

9. A method of treating intraocular pressure comprising the topical ocular administration to a patient in need of such treatment of an effective intraocular pressure lowering amount of a compound as defined in claim 1.

10. The method of claim 9 wherein the compound is as defined in claim 2.

11. The method of claim 9 wherein the compound is as defined in claim 3.

12. The method of claim 9 wherein the compound is as defined in claim 4.

* * * * *